US012653759B2

(12) United States Patent
Babineau

(10) Patent No.: US 12,653,759 B2
(45) Date of Patent: Jun. 16, 2026

(54) SYSTEMS AND METHODS FOR THE PRODUCTION OF SUPPOSITORY COMPOUNDS

(71) Applicant: Thomas Babineau, Circle Pines, MN (US)

(72) Inventor: Thomas Babineau, Circle Pines, MN (US)

( * ) Notice: Subject to any disclaimer, the term of this patent is extended or adjusted under 35 U.S.C. 154(b) by 171 days.

(21) Appl. No.: 18/362,246

(22) Filed: Jul. 31, 2023

(65) Prior Publication Data

US 2024/0033184 A1     Feb. 1, 2024

Related U.S. Application Data

(60) Provisional application No. 63/393,683, filed on Jul. 29, 2022.

(51) Int. Cl.
*A61J 3/08*          (2006.01)
*A61M 31/00*       (2006.01)
(52) U.S. Cl.
CPC .............. *A61J 3/08* (2013.01); *A61M 31/007* (2013.01); *A61M 2207/10* (2013.01)
(58) Field of Classification Search
CPC ..... A61J 3/08; A61M 31/007; A61M 2207/10
See application file for complete search history.

(56) References Cited

U.S. PATENT DOCUMENTS

| | | | | | |
|---|---|---|---|---|---|
| 2,932,386 | A | | 4/1960 | Ushkow | |
| 3,059,766 | A | * | 10/1962 | Jordt | A61J 3/08 206/529 |
| 3,104,665 | A | * | 9/1963 | Towns | A61J 3/08 206/529 |
| 4,537,311 | A | * | 8/1985 | Wilkinson | A61J 3/08 206/529 |
| 2015/0265820 | A1 | * | 9/2015 | Ensign | A61B 50/30 206/572 |

OTHER PUBLICATIONS

Dillingh, J., Smith, J. (2015). Containers. In: Bouwman-Boer, Y., Fenton-May, V., Le Brun, P. (eds) Practical Pharmaceutics. Springer, Cham. https://doi.org/10.1007/978-3-319-15814-3_24 (Year: 2015).*

* cited by examiner

*Primary Examiner* — JaMel M Nelson
*Assistant Examiner* — Erica Hartsell Funk
(74) *Attorney, Agent, or Firm* — UNDERWOOD & ASSOCIATES, LLC

(57)          ABSTRACT

A suppository mold includes an elongate reservoir having a shape of a suppository, a cap member hingedly connected to the reservoir on a first end portion of the reservoir and a flexible flat blade member disposed on a second end portion of the reservoir, opposite the first end portion. The reservoir comprises a malleable dome-shaped end portion adjacent said flexible flat blade member.

18 Claims, 2 Drawing Sheets

IA

125

105

SC

IA

SC

SYSTEMS AND METHODS FOR THE PRODUCTION OF SUPPOSITORY COMPOUNDS

REFERENCE TO RELATED APPLICATIONS

This application claims priority to and the benefit under 35 USC § 119(e) of U.S. Provisional Patent Application No. 63/393,683 filed on Jul. 29, 2022, entitled "Systems and Methods for the Production of Suppository Compounds", the contents of which are incorporated by reference in their entirety as if fully set forth herein.

TECHNICAL FIELD

This disclosure relates to systems and methods for the production of suppository compounds. In particular, this disclosure relates to a suppository mold including a sealable main reservoir, the main reservoir including a malleable, dome-shaped end portion and a flexible tab member integral with, or attached to the dome-shaped end portion that cooperatively provide the capability of urging a suppository compound formed within the main reservoir into a suppository insertion applicator.

BACKGROUND

Suppositories can be prepared by methods such as hand rolling, compression molding and fusion molding. The first method involves mixing an active ingredient in a cocoa butter base. The mixture is rolled into a cylindrical shape which is then cut into pieces that are rolled (or pointed) on one end to produce a conical shape.

Compression molding involves mixing an active ingredient with a supply of grated suppository base which is then forced into a compression mold. In this approach, the capacity of the molds is normally determined by compressing an amount of the base into a die and weighing the finished suppository.

Fusion molding involves melting the suppository base, then dispersing or dissolving one or more active compounds into the melted base; the mixture is then poured into a mold and left to cool. When the mixture has congealed or solidified, the resulting suppository is removed and prepared for use.

All of the above methods produce suppository products that can melt, leak, deform and/or deteriorate in warm climates, especially during storage and transport without the use of special heat sealing equipment, which can be costly and complex. Furthermore, it can be difficult to prepare different sized suppositories, or suppositories of different ingredient-to-base ratios without altering machine processes which can also be costly and time-consuming.

Accordingly, a suppository mold and container combination capable of withstanding preparation, transportation and storage in warm climates without deteriorating, melting, deforming or leaking, and that can be easily prepared and dosed for different sized delivery vehicles is an unmet need in the art.

SUMMARY

In general, a suppository mold and method of use is disclosed. In one exemplary embodiment, a suppository mold includes a main chamber for receiving suppository ingredients including a base mixture and one or more active compounds, e.g., pharmaceutical compositions. The size, shape and volume of the main chamber can be varied to accommodate different sizes of suppositories and is fitted with a sealing cap that can be opened by the end user to retrieve the suppository before use.

In one exemplary embodiment, a mold assembly for the production of a suppository compound includes an elongate reservoir having an open end and a closed end opposite said open end, a cap member hingedly connected proximal to said open end of said reservoir; and a flat blade member disposed on said closed end of said reservoir. The elongate reservoir comprises a rounded, or dome-shaped end portion adjacent said flat blade member. The elongate reservoir can have a volume sufficient for producing a rectal or vaginal suppository. For example, the mold volume can be between about 1.0 mL and about 5.0 mL. The elongate reservoir can have a length between 0.75-2.5 inches; the elongate reservoir can have a cross-section diameter of about 0.5 centimeter to about 2.0 centimeters.

In one embodiment, the cap member includes a plug of complimentary shape and size to allow said plug to be inserted into, and thereby seal said open end of said elongate reservoir. The plug can include a circumferential ring protrusion; the open end of said elongate reservoir can include a circumferential ring recess complementary to said ring protrusion, and the ring protrusion and said ring recess can cooperate to secure said cap when said mold assembly is in a closed and sealed configuration.

In one embodiment, the mold assembly further includes a table member, said table member can include at least one slot for receiving and supporting said flat blade member. The at least one slot can have a slot width substantially equal to a thickness of said flat blade member.

In one embodiment, the elongate reservoir further includes one or more exteriorly-disposed fin members that connect a plurality of said elongate reservoirs in series.

In one embodiment, the open end of said elongate reservoir is configured to couple to a suppository insertion applicator.

In one embodiment, the dome-shaped end is malleable. In a related embodiment, the dome-shaped end portion has a material thickness that is less than the material thickness of the remainder of the elongate reservoir.

In one embodiment, the elongate reservoir is formed of a material that is impervious to compounds used for suppository base matrices.

In one embodiment, the tab member is flexible. The tab member and said dome-shaped end portion can be configured to cooperatively urge a solidified suppository compound formed in the interior of said elongate reservoir into a suppository insertion applicator.

In various embodiments, the elongate reservoir further includes one or more markings or indicia that indicate a calibrated volume fill level.

In another exemplary embodiment, a method of producing a suppository is provided. The method includes depositing a suppository base matrix into an elongate reservoir as described in any of the preceding embodiments, optionally depositing one or more compounds into said elongate reservoir, or pre-mixing said one or more compounds with said suppository base matrix prior to said depositing said suppository base matrix into said elongate reservoir, and capping said elongate reservoir with said cap member.

Certain advantages of the systems and methods include providing specific volume molded containers of a shape appropriate for intended use, for example, 1.0 mL, 1.3 ml, 2.0 ml, 2.25 ml, 2.5 ml, 3.0 ml, 3.5 ml, 4.0 mL, 4.5 mL, 5.0 mL, among others; the mold includes a hinged cap for easily sealing once filled that is recessed to a specific height so if contents liquify, the overall dose will not lose its shape once the temperature is reduced; the mold includes a wide opening for easier and faster filling than traditional molds and a ring locking feature on the inside of the cap secures the cap to the main chamber to prevent leaking; the mold shape includes a rounded, tapered bottom with a protruding flexible blade allowing the user to easily extract the dose from the container by flexing the blade and pinching the tapered end, which reduces the amount of handling required by the end user; the wall thickness of the mold can be varied to prevent deformation of the suppository mold and allows for the tapered end to remain flexible for dose extraction; the shape of the mold and the design of the cap receiving feature allows a user to attach an insertion applicator and squeeze the dose in the right orientation into the insertion applicator without handling the dose which is required when using traditional designs; the flat blade protruding from the tapered bottom that allows the mold to stand in the upright orientation to be filled; the mold can be stacked with other molds for optimized packaging and reduced shipping/storing costs; among others.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings, which may not necessarily be to scale, in which like references indicate similar elements, and in which.

DETAILED DESCRIPTION OF ILLUSTRATIVE EMBODIMENTS

Figure 1:
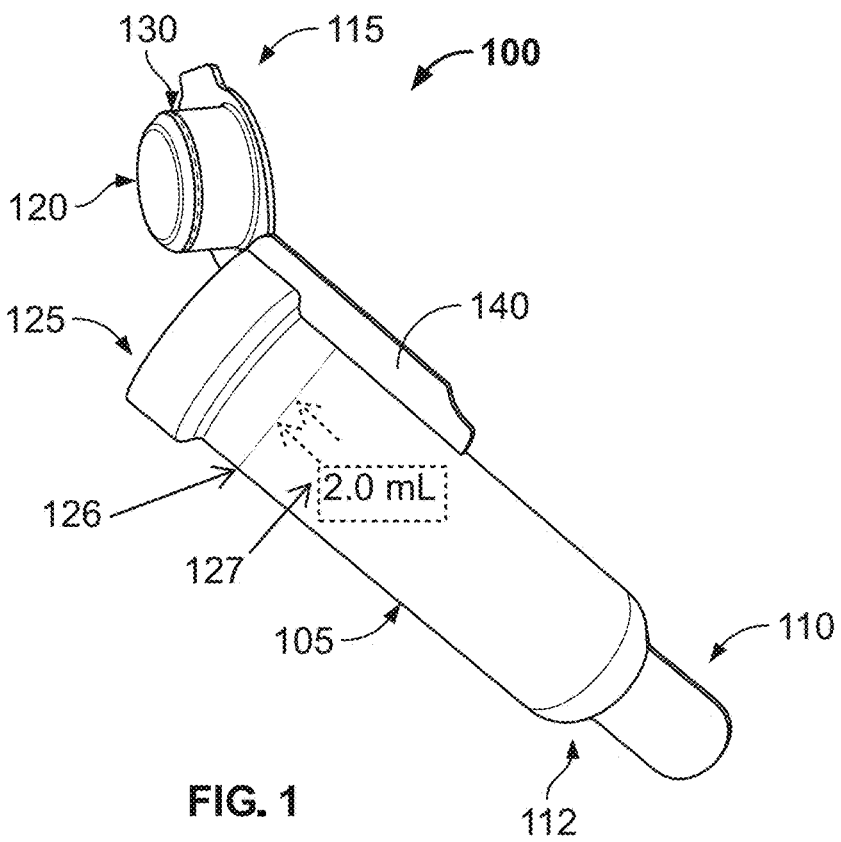
FIG. 1 illustrates a suppository mold container according to one embodiment.
Figure 2:
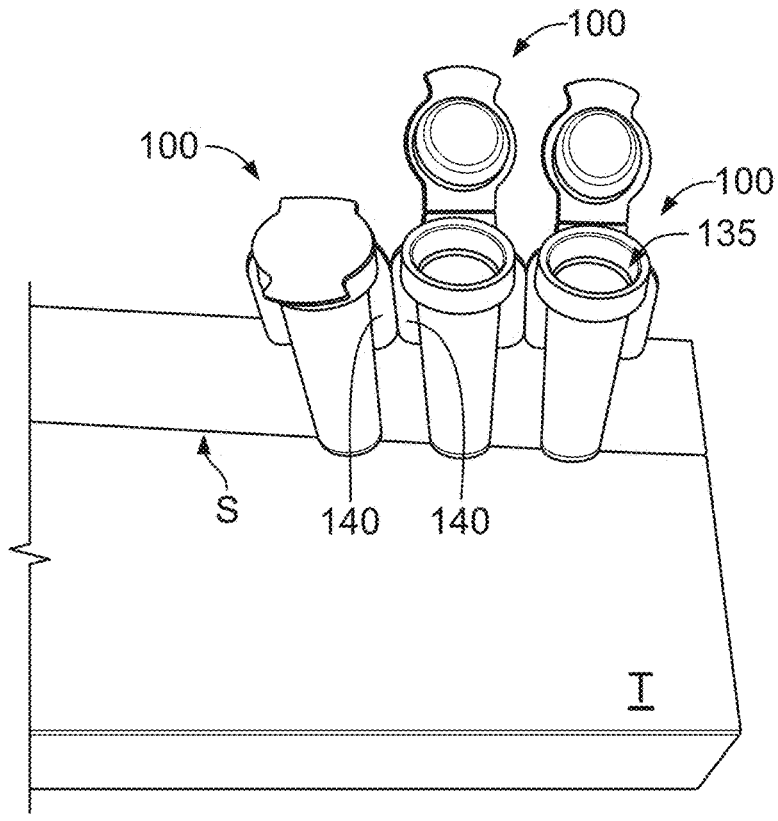
FIG. 2 illustrates a series of linked suppository molds supported by a table, according to one embodiment.

FIG. 1 is a suppository mold container (hereinafter 'container') 100 according to one embodiment. In this embodiment, the container 100 includes a main reservoir 105 for receiving a base compound and at least one active ingredient to form a suppository. The bottom portion of the container 100 terminates in a flat blade 110 configuration for removing a suppository compound from the main reservoir as described herein, and also so that the container 100 can be placed within a slot S of a holding table T (FIG. 2) for ease of filling each reservoir 105. In this example, the slot S has a width to accommodate the blade 110 so that a series of containers 100 can be placed in a secure, upright configuration as illustrated in FIG. 2.

In this embodiment, the container 100 further includes a cap 115 that is configured to frictionally engage a corresponding opening 125 at the top portion of the main reservoir 105 that is used to close and seal the container 100. In this embodiment, the cap 115 includes a plug portion 120, which itself includes a circumferential ring protrusion 130 that snaps into locking engagement with a complementary ring recess 135 in the opening 125 as shown. Plug portion 120 acts to seal the contents of the reservoir 105 by plugging the main reservoir opening 125 when in the closed position, as illustrated by the container 100 on the far left of the table T as exemplified in FIG. 2.

In this embodiment, the bottom portion 112 of the reservoir 105 is preferably rounded, or dome shaped and malleable. The dome shape can not only aid in comfortable insertion for the user, but also provides a convenient and mess-free way to extract a suppository from the reservoir 105 prior to use, by flexing the blade 110 and pinching the malleable dome portion 112. After extraction, the suppository can be placed into a traditional applicator without touching or handling by the user, as is the case for traditional suppository packaging.

In this and other embodiments, the container 100 can be sized for intended use and dosage. For example, and without limitation, the container 100 can be sized and configured to hold a suppository volume of 1.0 mL, 1.3 mL, 2.0 mL, 2.25 mL, 2.5 mL, 3.0 mL, 3.5 mL, 4.0 mL, 4.5 mL, 5.0 mL, etc. Such flexibility in sizing allows a proper dosage and appropriate administration for different user populations, e.g., children, adults, geriatric patients, etc.

The container can be used to create a suppository containing a desired amount of suppository base and one or more active ingredients. In one such example, a base matrix of a suppository material, such as liquified cocoa butter can first be added to the reservoir portion 105. Next, an active ingredient of the suppository can be added to the reservoir 105. Alternatively, a mixture of the base and at least one active ingredient can be pre-mixed and added to the reservoir 105, or the active ingredient may be added prior to the base matrix. Next, the reservoir 105 can be closed and sealed by urging the cap 115 into the reservoir opening 125 such that circumferential ring protrusion 130 snaps into locking engagement with the corresponding ring recess 135 within the opening 125. Next, the mixture of matrix base and active ingredient can be cooled, thereby forming the suppository.

Figure 3:
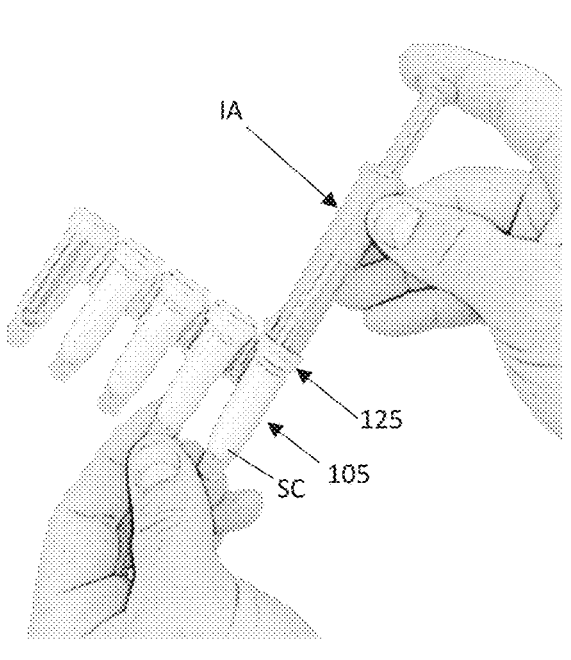
FIG. 3 illustrates the extraction of a suppository compound from a suppository mold, according to one embodiment.
Figure 4:
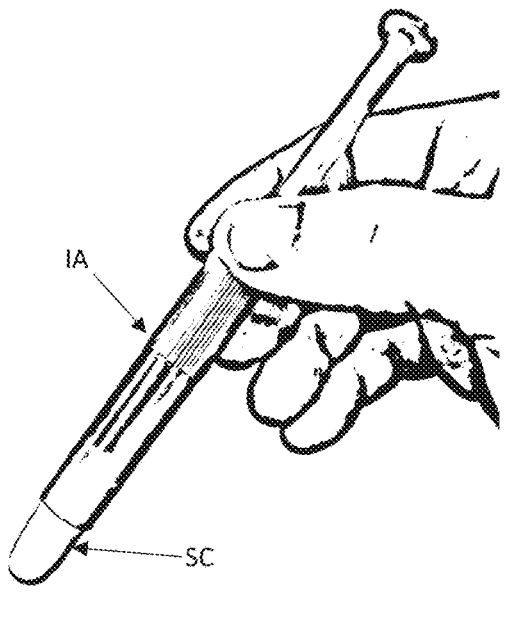
FIG. 4 illustrates a suppository insertion applicator ready for use, according to one embodiment.

Referring to FIGS. 3 and 4, a user may extract the resultant suppository compound by reversing the process. First, the user can open the reservoir 105 by decoupling the cap portion 115 from the opening 125. Next, the user can grasp the blade portion 110 and gently bend, urging the suppository from the reservoir 105 followed by pinching the dome shaped portion 112. The opening 125 can then be coupled to an insertion applicator IA (FIG. 3); the suppository compound SC can then be inserted directly into the insertion applicator IA designed for use with suppositories and used as directed (FIG. 4).

In this and other embodiments, the ability to seal the contents of a suppository matrix within the reservoir 105 provides certain advantages. For example, in warm climates, suppositories can liquify or melt, as the base substance is oftentimes a material such as cocoa butter that has a low melting point. The container 100 provided herein guarantees that the intended shape of the suppository, defined by the size and shape of the reservoir 105, will properly re-form once the container 100 is cooled down to a temperature where the base matrix will solidify. Thus, even if a user receives a suppository within container 100 that has been melted by, e.g., shipping or leaving the suppository in a warm environment, the user can re-form the suppository by placing the container 100 in a refrigerator or other cool environment.

Another advantage rests in the wide opening of the opening 125 leading to the reservoir 105. Such an opening provides ease of filling compared to traditional methods, and the sealable cap 115 allows for quick and reliable closing of the container 100 without the use of special sealing equipment once all ingredients have been added.

In this and other embodiments, the container 100 can include indicia, markings or other features. For example, in this embodiment, the container 100 includes a calibrated dose fill mark 126 and a corresponding identification 127 of the volume of the reservoir 105. Such information can provide consistent visual fill accuracy by a pharmacist or other person or process creating the suppository compound. Other markings and indicia can include, without limitation, suppository compound ingredients, expiration dates, branding or other information. In this and other embodiments, containers 100 can be of different colors to visually indicate certain reservoir volumes.

In this and other embodiments, the thickness of the reservoir wall, interior surface features, and material composition of the container 100 can be selected to optimize temperature tolerance, surface slippage, flexibility, quality requirements, extractability of the suppository, purity, UV inhibition and other factors as desired. In one embodiment, the container is formed of a resilient plastic that resists crushing, denting or bending during shipping and handling.

In this and other embodiments, the containers 100 can be serially-attached by break-away side fin members 140. The fin members 140 connect multiple containers in series which can be stood upright with the cooperative use of the table T illustrated in FIG. 2. In this embodiment, the table T includes a slot S that has a width substantially equal to, or slightly greater than the thickness of the container blade 110 that allows for insertion of one or more containers. For example, the slot width can be between the thickness of the blade plus 10% of the thickness of the blade. The container 100/table T combination can be useful for mass production of suppository compounds as well as individual preparation, e.g., by a pharmacist. In this embodiment, the fin members 140 are configured to allow each container 100 to be separated by, e.g., twisting, snapping, bending or breaking the fin members 140 between containers 100.

A number of illustrative embodiments have been described. Nevertheless, it will be understood that various modifications may be made without departing from the spirit and scope of the various embodiments presented herein. Accordingly, other embodiments are within the scope of the following claims.

What is claimed is:

1. A mold assembly for the production of a suppository compound, comprising:
   an elongate reservoir having an open end and a closed end opposite said open end;
   a cap member hingedly connected proximal to said open end of said reservoir; and
   a flat blade member disposed on said closed end of said reservoir;

wherein said elongate reservoir comprises a rounded or dome-shaped end portion adjacent said flat blade member.

2. The mold assembly of claim 1, wherein said elongate reservoir has a volume sufficient for producing a rectal or vaginal suppository.

3. The mold assembly of claim 2, wherein said volume is between about 1.0 mL and about 5.0 mL.

4. The mold assembly of claim 2, wherein said elongate reservoir has a length between 0.75-2.5 inches.

5. The mold assembly of claim 2, wherein said elongate reservoir has a cross-section diameter of about 0.5 centimeter to about 2.0 centimeters.

6. The mold assembly of claim 1, wherein said cap member comprises a plug of complimentary shape and size to allow said plug to be inserted into, and thereby seal said open end of said elongate reservoir.

7. The mold assembly of claim 6, wherein said plug comprises a circumferential ring protrusion, said open end of said elongate reservoir comprises a circumferential ring recess complementary to said ring protrusion, and wherein said ring protrusion and said ring recess cooperate to secure said cap when said mold assembly is in a closed and sealed configuration.

8. The mold assembly of claim 1, further comprising a table member, said table member comprising at least one slot for receiving and supporting said flat blade member.

9. The mold assembly of claim 8, wherein said at least one slot has a slot width substantially equal to a thickness of said flat blade member.

10. The mold assembly of claim 1, wherein said elongate reservoir further comprises one or more exteriorly-disposed fin members that connect a plurality of said elongate reservoirs in series.

11. The mold assembly of claim 1, wherein said open end of said elongate reservoir is configured to couple to a suppository insertion applicator.

12. The mold assembly of claim 1, wherein said rounded or dome-shaped end is malleable.

13. The mold assembly of claim 12, wherein said rounded or dome-shaped end portion has a material thickness that is less than the material thickness of the remainder of the elongate reservoir.

14. The mold assembly of claim 1, wherein said elongate reservoir is formed of a material that is impervious to compounds used for suppository base matrices.

15. The mold assembly of claim 1, wherein said tab-flat blade member is flexible.

16. The mold assembly of claim 15, wherein said tab-flat blade member and said rounded or dome-shaped end portion are configured to cooperatively urge a solidified suppository compound from the interior of said elongate reservoir into a suppository insertion applicator.

17. The mold assembly of claim 1, wherein said elongate reservoir further comprises one or more markings or indicia that indicate a calibrated volume fill level.

18. A method of producing a suppository, comprising:
   depositing a suppository base matrix into the elongate reservoir of claim 1;
   optionally depositing one or more compounds into said elongate reservoir, or pre-mixing said one or more compounds with said suppository base matrix prior to said depositing said suppository base matrix into said elongate reservoir; and
   capping said elongate reservoir with said cap member.

* * * * *